United States Patent
Zhang et al.

(10) Patent No.: US 8,417,355 B2
(45) Date of Patent: Apr. 9, 2013

(54) CARDIAC FORCE SENSOR AND METHODS OF USE

(75) Inventors: Yongxing Zhang, Irvine, CA (US); Yunlong Zhang, Mounds View, MN (US); Xuan Wei, Plymouth, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 153 days.

(21) Appl. No.: 12/940,172

(22) Filed: Nov. 5, 2010

(65) Prior Publication Data

US 2011/0046496 A1   Feb. 24, 2011

Related U.S. Application Data

(62) Division of application No. 11/559,702, filed on Nov. 14, 2006, now Pat. No. 7,848,822.

(51) Int. Cl.
*A61N 1/05* (2006.01)
(52) U.S. Cl.
USPC .......................................................... 607/122
(58) Field of Classification Search .............. 607/24–25, 607/1–5, 17
See application file for complete search history.

(56) References Cited

U.S. PATENT DOCUMENTS

| | | |
|---|---|---|
| 3,724,274 A | 4/1973 | Millar |
| 3,958,588 A | 5/1976 | Huddle |
| 3,971,364 A | 7/1976 | Fletcher et al. |
| 4,979,510 A | 12/1990 | Franz et al. |
| 5,255,679 A | 10/1993 | Imran |
| 5,300,106 A | 4/1994 | Dahl et al. |
| 5,353,800 A | 10/1994 | Pohndorf et al. |
| 5,405,337 A | 4/1995 | Maynard |
| 5,423,883 A | 6/1995 | Helland |
| 5,496,361 A | 3/1996 | Moberg et al. |
| 5,589,563 A | 12/1996 | Ward et al. |
| 5,607,996 A | 3/1997 | Nichols et al. |
| 5,628,777 A | 5/1997 | Moberg et al. |
| 5,683,447 A | 11/1997 | Bush et al. |
| 5,693,081 A | 12/1997 | Fain et al. |
| 5,782,841 A | 7/1998 | Ritz et al. |
| 5,800,497 A | 9/1998 | Bakels et al. |
| 5,843,153 A | 12/1998 | Johnston et al. |
| 5,938,603 A | 8/1999 | Ponzi |

(Continued)

FOREIGN PATENT DOCUMENTS

| | | |
|---|---|---|
| WO | WO-9502359 A1 | 1/1995 |
| WO | WO-9503086 A2 | 2/1995 |

(Continued)

OTHER PUBLICATIONS

"U.S. Appl. No. 11/559,702, Final Office Action mailed Apr. 16, 2010", 15 pgs.

(Continued)

*Primary Examiner* — Carl H Layno
*Assistant Examiner* — Paula J Stice
(74) *Attorney, Agent, or Firm* — Schwegman Lundberg & Woessner, P.A.

(57) ABSTRACT

A method and apparatus permit sensing one or more forces exerted by one or more portions of a heart. A force transducer and displacement sensor are disclosed. A movement of one or more portions of a heart can be translated into one or more signals indicative of force. These signals can be used to provide information such as to diagnose or treat one or more conditions.

21 Claims, 13 Drawing Sheets

U.S. PATENT DOCUMENTS

| | | | |
|---|---|---|---|
| 5,991,661 | A | 11/1999 | Park et al. |
| 6,205,359 | B1 | 3/2001 | Boveja |
| 6,215,231 | B1 | 4/2001 | Newnham et al. |
| 6,254,568 | B1 | 7/2001 | Ponzi |
| 6,301,507 | B1 | 10/2001 | Bakels et al. |
| 6,324,414 | B1 | 11/2001 | Gibbons et al. |
| 6,327,492 | B1 | 12/2001 | Lemelson |
| 6,332,089 | B1 | 12/2001 | Acker et al. |
| 6,340,588 | B1 | 1/2002 | Nova et al. |
| 6,514,237 | B1 | 2/2003 | Maseda |
| 6,522,909 | B1 | 2/2003 | Garibaldi et al. |
| 6,699,186 | B1 | 3/2004 | Wolinsky et al. |
| 6,809,462 | B2 | 10/2004 | Pelrine et al. |
| 6,871,088 | B2 | 3/2005 | Chinchoy |
| 6,881,516 | B2 | 4/2005 | Aamodt et al. |
| 6,915,162 | B2 | 7/2005 | Noren et al. |
| 6,939,313 | B2 | 9/2005 | Saadat et al. |
| 6,980,866 | B2 | 12/2005 | Yu et al. |
| 7,072,703 | B2 | 7/2006 | Zhang et al. |
| 7,203,541 | B2 | 4/2007 | Sowelam et al. |
| 2002/0111662 | A1 | 8/2002 | Iaizzo et al. |
| 2002/0116043 | A1 | 8/2002 | Garibaldi et al. |
| 2003/0055360 | A1 | 3/2003 | Zeleznik |
| 2003/0065373 | A1 | 4/2003 | Lovett et al. |
| 2003/0139794 | A1 | 7/2003 | Jenney et al. |
| 2004/0049255 | A1 | 3/2004 | Jain et al. |
| 2004/0127889 | A1 | 7/2004 | Zhang et al. |
| 2004/0225332 | A1 | 11/2004 | Gebhardt et al. |
| 2005/0240233 | A1 | 10/2005 | Lippert et al. |
| 2005/0288727 | A1 | 12/2005 | Penner |
| 2006/0041298 | A1 | 2/2006 | Yu et al. |
| 2006/0178586 | A1 | 8/2006 | Dobak, III |
| 2008/0114256 | A1 | 5/2008 | Zhang et al. |
| 2008/0255629 | A1 | 10/2008 | Jenson et al. |
| 2008/0262473 | A1 | 10/2008 | Kornblau et al. |

FOREIGN PATENT DOCUMENTS

| | | |
|---|---|---|
| WO | WO-9503086 A3 | 2/1995 |
| WO | WO-2005011803 A2 | 2/2005 |
| WO | WO-2005118056 A2 | 12/2005 |
| WO | WO-2005118056 A3 | 12/2005 |

OTHER PUBLICATIONS

"U.S. Appl. No. 11/559,702, Non-Final Office Action mailed Nov. 9, 2009", 15 pgs.

"U.S. Appl. No. 11/559,702, Notice of Allowance mailed Jul. 30, 2010", 8 pgs.

"U.S. Appl. No. 11/559,702, Response filed Feb. 9, 2010 to Non Final Office Action mailed Nov. 9, 2009", 15 pgs.

"U.S. Appl. No. 11/559,702, Response filed Jul. 15, 2010 to Final Office Action mailed Apr. 16, 2010", 15 pgs.

"U.S. Appl. No. 11/559,702, Response filed Sep. 1, 2009 to Restriction Required mailed Aug. 13, 2009", 10 pgs.

"U.S. Appl. No. 11/559,702, Restriction Requirement mailed Aug. 13, 2009", 7 pgs.

"U.S. Appl. No. 11/559,702, Supplemental Notice of Allowability Mailed Oct. 14, 2010", 5 pgs.

Bennett, T., et al., "Development of implantable devices for continuous ambulatory monitoring of central hemodynamic values in heart failure patients", Pacing Clin Electrophysiol, vol. 28, No. 6, (Jun. 2005), 573-584.

Bongiorni, M. G, et al., "Is local myocardial contractility related to endocardial acceleration signals detected by a transvenous pacing lead?", Pacing Clin Electrophysiol, (11 Pt 2), (Nov. 1996), 1682-1688.

Measurand Inc., "S700 & S710 Joint Angle ShapeSensor Spec Sheet, S720 Miniature Joint Angle Shape Sensor, S290 12 Bit Data Acquisition System", www.measurand.com/products/shapesensors-literature.html, (Sep. 12, 2002), 5 pgs.

Measurand Inc., "ShapeRecorder Software User Instructions", www.measurand.com, (2002), 66 pgs.

Measurand Inc., "ShapeTape Manual", Cautions, Description of Hardware and software options, Description and use of hardware, Instructions for ShapeWare software, Theory, (Aug. 15, 2003), i/143-114/143, I-XIX.

SRI International, "Research of Artificial Muscles", www.mmc.or.jp/info/magazine/14e/act/11/sri1.htm, (Mar. 1996), 6 pgs.

Theres, Heinz P, et al., "Detection of acute myocardial ischemia during percutaneous transluminal coronary angioplasty by endocardial acceleration.", Pacing Clin Electrophysiol., vol. 27, No. 5, (May 2004), 621-625.

www.designinsite.dk, "Material Dielectric Eastomers", web.archive.org/web/20010306073022/www.designinsite.dk/htmsider/insptour.htm, Copyright 1996-2003 Torben Lenau. This page is part of Design inSite, (Copyright 1996-2003), 2 pgs.

CARDIAC FORCE SENSOR AND METHODS OF USE

CROSS-REFERENCE TO RELATED APPLICATIONS

This application is a Division of U.S. application Ser. No. 11/559,702, filed on Nov. 14, 2006, now issued as U.S. Pat. No. 7,848,822, the benefit of priority of which is claimed herein, and which is incorporated herein by reference in its entirety.

TECHNICAL FIELD

This document relates generally to medical systems, devices, and methods, and particularly, but not by way of limitation, to a cardiac force sensor and methods of use.

BACKGROUND

When functioning properly, the human heart maintains a normal sinus rhythm. Its sinoatrial node generates intrinsic electrical cardiac signals that depolarize the atria, causing atrial contractions. Its atrioventricular node then passes the intrinsic cardiac signal to depolarize the ventricles, causing ventricular contractions.

A normal heart is capable of pumping adequate blood throughout the body's circulatory system. However, some people have irregular cardiac rhythms, referred to as cardiac arrhythmias. Moreover, some patients have poor spatial coordination of heart contractions. For these and other reasons, impaired blood circulation may result. For such patients, a cardiac rhythm management (CRM) system may be used to improve the rhythm or spatial coordination of heart contractions. Such systems often include a CRM device that is implanted in the patient to deliver therapy to the heart.

Cardiac rhythm management systems include, among other things, pacemakers, also referred to as pacers. Pacers deliver timed sequences of low energy electrical stimuli, called pacing pulses, to the heart, such as via an intravascular lead wire or catheter (referred to as a "lead") having one or more electrodes disposed in or about the heart. Heart contractions are initiated in response to such pacing pulses (this is referred to as "capturing" the heart). By properly timing the delivery of pace pulses, the heart can be induced to contract in proper rhythm, greatly improving its efficacy as a pump. Pacers are often used to treat patients with bradyarrhythmias, that is, hearts that beat abnormally slowly. Such pacers may also coordinate atrial and ventricular contractions to improve pumping efficacy.

Cardiac rhythm management systems also include cardiac resynchronization therapy (CRT) devices for spatially coordinating heart depolarizations for improving pumping efficacy. For example, a CRT device may deliver appropriately timed pace pulses to different locations of the same heart chamber to better coordinate the contraction of that heart chamber, or the CRT device may deliver appropriately timed pace pulses to different heart chambers to achieve better synchronization.

Cardiac rhythm management systems also include defibrillators that are capable of delivering higher energy electrical stimuli to the heart. Such defibrillators include cardioverters, which typically synchronize the delivery of such stimuli to sensed intrinsic heart activity signals. Defibrillators are often used to treat patients with tachyarrhythmias, that is, hearts that beat abnormally quickly. Such too-fast heart rhythms can also cause impaired blood circulation. A defibrillator is capable of delivering a high energy electrical stimulus that is sometimes referred to as a defibrillation countershock, also referred to simply as a "shock." The shock terminates the tachyarrhythmia, allowing the heart to reestablish a normal rhythm for the improved pumping of blood. In addition to pacers, CRT devices, and defibrillators, CRM systems also include CRM devices that combine these functions, as well as monitors, drug delivery devices, and any other implantable or external systems or devices for diagnosing or treating the heart. Cardiac rhythm management systems often include external local or remote user interfaces (sometimes referred to as "programmers" or "patient management systems") for programming one or more therapy control or other parameters of an implantable cardiac rhythm management device, or for receiving physiological or other data communicated from the implantable cardiac rhythm management device. Accurate measurement of hemodynamic conditions is helpful to developing an effective cardiac rhythm management system.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Sensing electrical cardiac conductions may not provide the desired information about a cardiac contraction. In certain circumstances, it is useful to be able to detect mechanical indications of heart contractions, either in addition to or as an alternative to detecting the electrical cardiac conduction of heart contractions. The present inventors have recognized a need for improved techniques for measuring, monitoring or trending of cardiac conditions, such as by sensing cardiac force.

Figure 1:
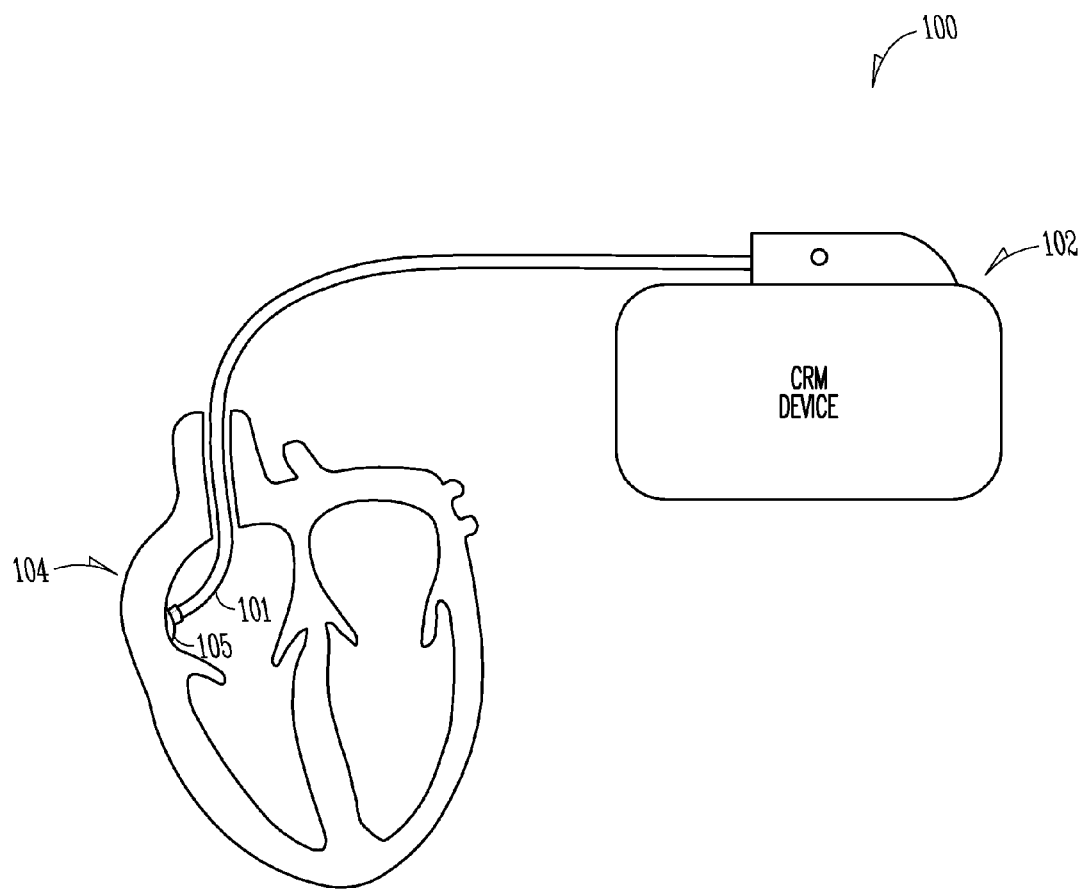
FIG. 1 illustrates generally portions of a Cardiac Rhythm Management (CRM) system and a heart.

FIG. 1 is a block diagram illustrating generally portions of a cardiac rhythm management (CRM) system 100 and portions of an environment in which it is used. In this example, the CRM system 100 includes an implantable CRM device 102. The CRM device 102 can be coupled to a heart 104, such as by using one or more leads 101 associated with heart 104. The leads 101 typically include electrodes to permit sensing one or more intracardiac signals or to permit delivering energy or other therapy. The device 102 is typically sized and shaped for being pectorally or abdominally implanted in a human patient. The leads 101 may include one or more electrodes 105. Examples of the electrodes 105 can include an intravascular electrode, an cardiac electrode, or an epicardial electrode. The electrodes 105 need not be located on a lead, for example, the electrodes 105 may include a housing or a header electrode located on a housing of device 102 or a header attached thereto, or any combination of the above. In certain examples, the lead 101 includes one or more cardiac force sensors adapted to sense one or more forces exerted by one or more portions of a heart.

Figure 2A:
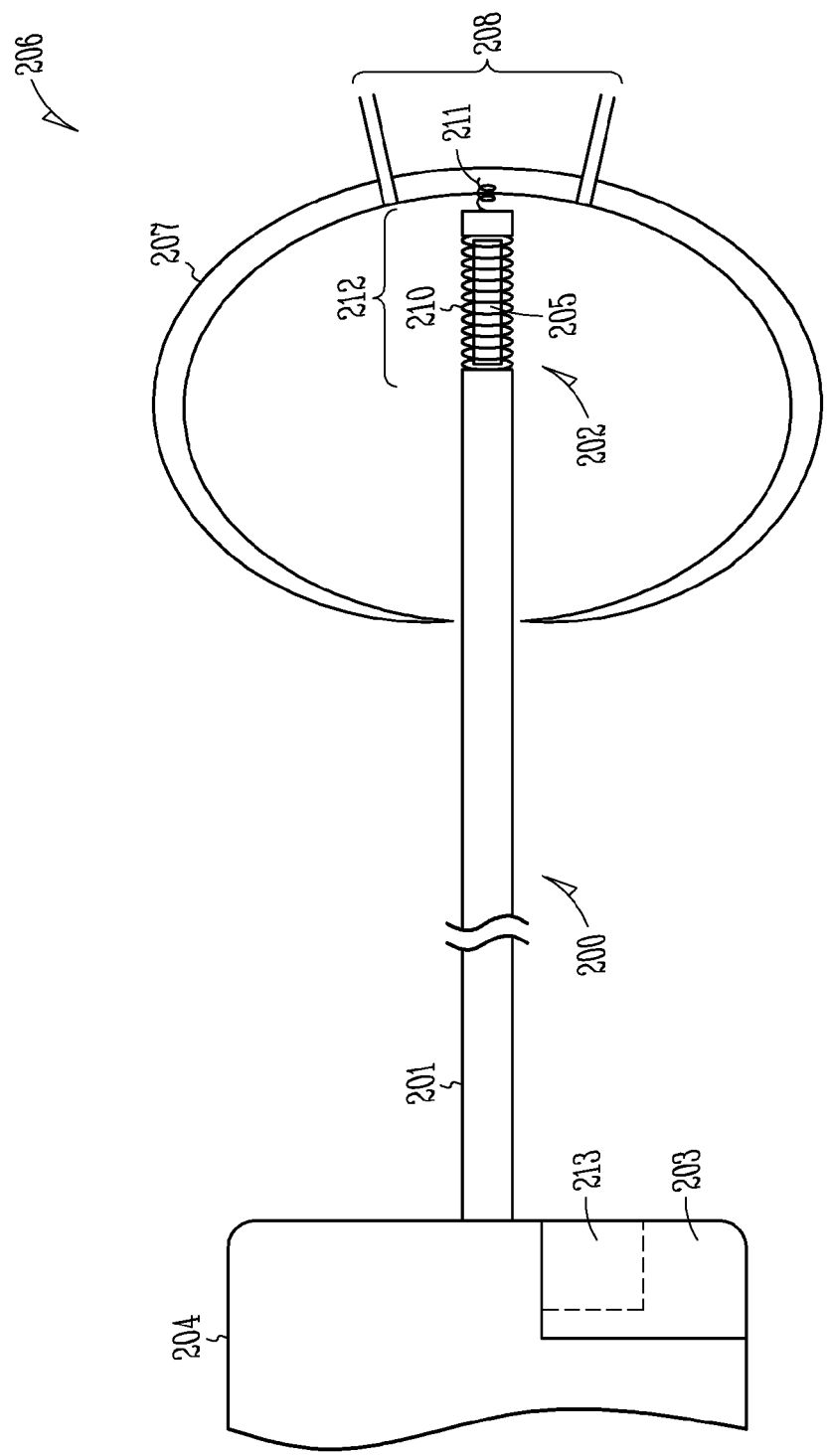
FIG. 2A illustrates generally portions of a CRM system adapted to sense cardiac force.

FIG. 2A illustrates an example of an apparatus adapted to measure one or more cardiac forces. In this example, a CRM system 206 includes an implantable medical device 204 with an electronics unit 203 and an intravascular lead 200. The proximal portion 201 of the lead 200 is adapted to be mechanically and communicatively coupled to the electronics unit 203 of the implantable medical device 204. The electronics unit 203 typically includes a controller 213 that receives cardiac force or other information from one or more leads 200. In certain examples, the controller 213 of the electronics unit 203 uses the force information to initiate or adjust a response, such as a delivered electrical energy or a delivered substance.

In the example of FIG. 2A, the distal portion 202 of the pacing, defibrillation, or other lead 202 is sized and shaped to be acutely or chronically located within a chamber or vasculature of the heart 207 or an ancillary vessel. In this example, the distal portion of the lead 202 includes or is attached to a force sensor 212. The force sensor 212 can be adapted to determine a cardiac force, such as from a displacement measured by a spring having a known spring constant. This information can be used to derive one or more other characteristics, such as pressure, torsion, acceleration, velocity, displacement, or any combination of these measurements.

In this example, the force sensor 212 includes a force transducer 210. The force transducer 210 includes a displacement sensor 205 and a spring or other contractile structure that contracts (or expands) in response to an applied force. To convert displacement into force, the contractile structure typically includes a specified linear or non-linear force-displacement relationship, such as a specified spring constant, for example. In the example of FIG. 2A, the force transducer 210 includes a spring as the contractile structure. In another example, the force transducer 210 includes a bellows as the contractile structure. The displacement sensor 205 can sense heart wall movement. The force transducer 210 uses the displacement sensor 205 to convert the sensed displacement into a signal indicative of a force due to the heart wall movement. Examples of a displacement sensor 205 can include, without limitation: a reluctance based displacement sensor, a fiber-optic displacement sensor, a piezoelectric displacement sensor, a strain gauge displacement sensor, and a capacitive displacement sensor. The lead 202 can optionally include a passive or active fixation mechanism 211, such as to immobilize or secure the distal portion of the lead 202 to at least one portion 208 of the heart 207. In the example of FIG. 2A, the fixation mechanism 211 includes an active fixation mechanism, such as a corkscrew-like structure. Other examples of fixation mechanisms include, without limitation: a barb, a harpoon-like structure, one or more tines, a pre-formed shape (e.g., bowed, spiral, J-shaped, etc.) or a hook.

The electronics unit 203 can be configured to determine an indication of cardiac force directly, or as a function of the sensed displacement, such as by using a controller, processor, or other circuit. In a linear displacement sensor example, since the spring constant of the contractile material is known, force can be determined as the multiplicative product of the spring constant and the sensed displacement. The electronics unit 203 can be separate from or integrated with the force sensor 212.

Figure 2B:
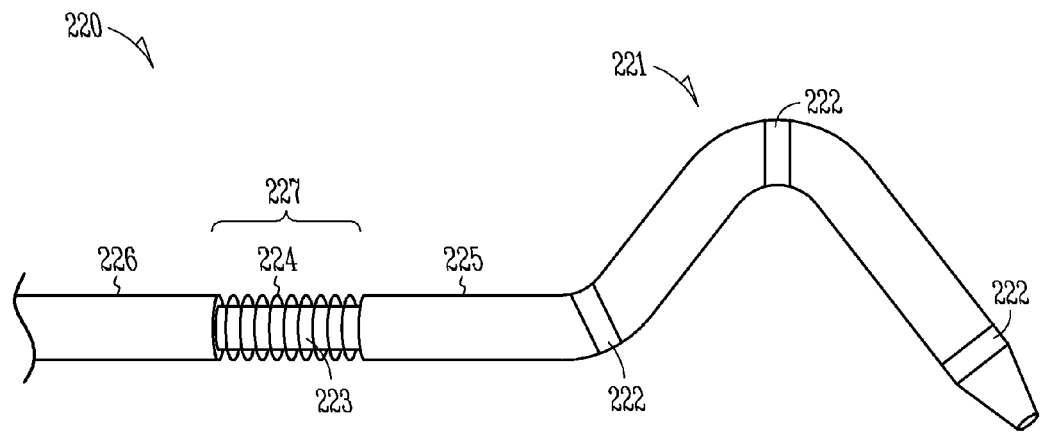
FIG. 2B illustrates generally portions of a CRM system adapted to sense cardiac force along the body of the lead.

FIG. 2B illustrates an alternative example of an apparatus adapted to measure one or more cardiac forces. In this example, a lead 220 includes a distal portion 221 and a proximal portion 226. The distal portion 221 includes one or more electrodes 222. In this example, a force sensor 227 is located on a lead body 225 between the distal portion 221 and proximal portion 226. In this example, the force sensor 227 includes a displacement sensor 223 and a force transducer 224 that converts the sensed displacement into a sensed signal indicative of force. In general, the force sensor 227 need not be located at the distal tip or distal portion 221 of the lead 220, but may include a force sensor 227 at any location along the lead body.

Figure 2C:
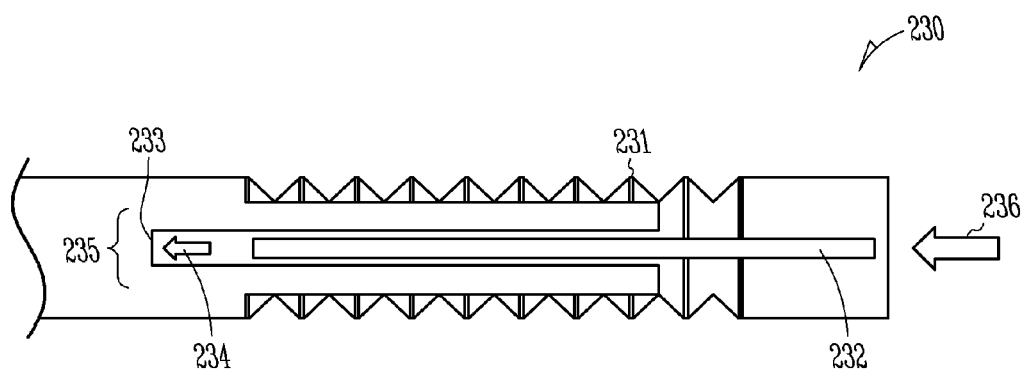
FIG. 2C illustrates an example, by way of illustration and not by way of limitation, of a force sensor.

FIG. 2C illustrates an example of an apparatus adapted to measure one or more cardiac forces. In this example, the force sensor 230 includes a displacement sensor 235 and a force transducer 231. In this example, the force transducer 231 includes a bellows. In this example, the displacement sensor 235 includes an example of a reluctance-based linear displacement sensor 235 including a piston-like core 232 and a lumen 233. In this example, when a force 236 is applied, the core 232 moves (e.g., displacement 234) within the lumen 233. This displacement can be converted into a signal indicative of force, such as by the specified force-displacement relationship of the force transducer 231 (such as, in this example, the spring constant of the bellows).

Figure 3:
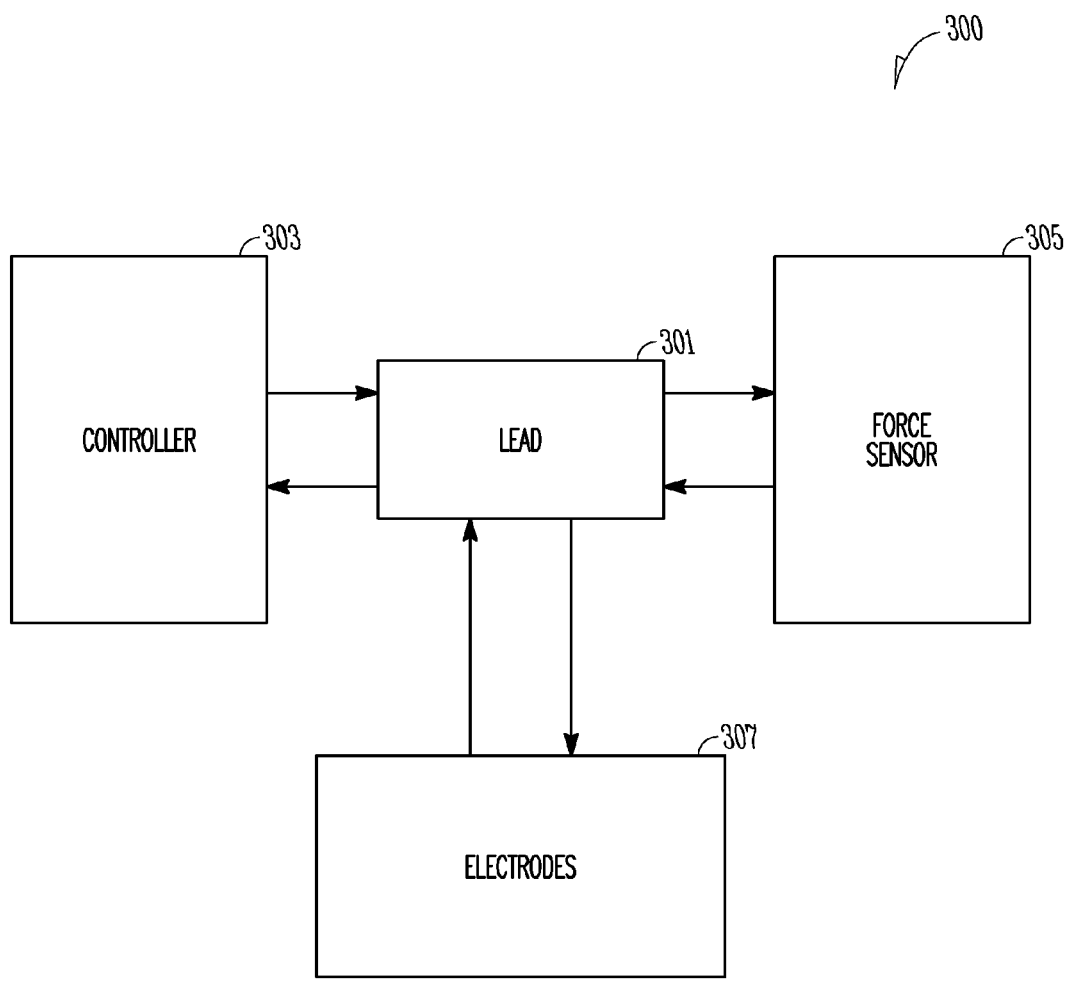
FIG. 3 illustrates an example of portions of a CRM system adapted to sense cardiac force.

FIG. 3 illustrates generally an example of portions of a CRM system 300 adapted to detect, monitor, or trend information about heart wall motion or cardiac force. In this example, the CRM system 300 includes one or more leads 301 with one or more force sensors 305, one or more electrodes 307, and a controller 303.

One or more of the leads 301 are adapted to communicate measurements taken by the one or more force sensors 305, and any electrical signals communicated with the one or more electrodes 307. In various examples, the controller 303 is adapted to initiate or adjust one or more responses, such as a delivered electrical energy or a delivered substance, based on one or more sensed forces and/or one or more other physiological parameters. As an example, the controller 303 may cycle through various parameter settings (e.g., electrode selection, pacing location, pacing rate, AV-delay, interventricular delay, intraventricular delay, or the like) to test how strongly the heart contracts in response to a particular combination of parameter settings. The parameter settings corresponding to the desired contraction or contraction pattern can then be selected for ongoing use. Such testing can be carried out recurrently or periodically, such as in case physiological conditions change so that the current parameter settings no longer obtain the desired heart contraction or contraction pattern. If so, the parameter settings can be adjusted as desired. The parameter settings need not be based exclusively on the sensed force; in other examples, the sensed force is just one factor among others in determining the parameter settings.

Figure 4:
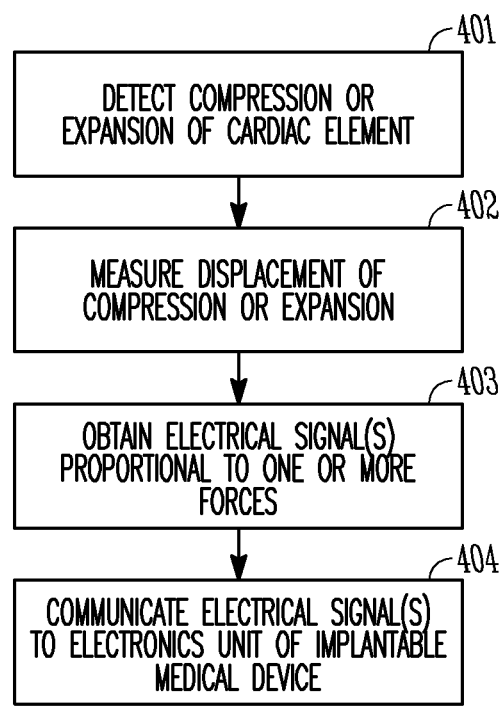
FIG. 4 illustrates an example of a method of sensing force.

FIG. 4 illustrates an example of a method of sensing one or more forces of at least one portion of a heart. At 401, an expansion or compression in response to a heart wall movement is detected by a cardiac element, such the force sensor 210. At 402, a resulting displacement is measured, such as using a displacement sensor 205. At 403, an electrical signal representative of the one or more sensed forces is obtained. The contraction or expansion involves a displacement that, via the spring constant, yields an indication of force. An electrical signal representative of the displacement is therefore indicative of one or more sensed forces exerted by one or more portions of the heart. At 404, the electrical signal indicative of one or more sensed forces is communicated, such as to the electronics unit 203 of an implantable medical device 204.

Figure 5A:
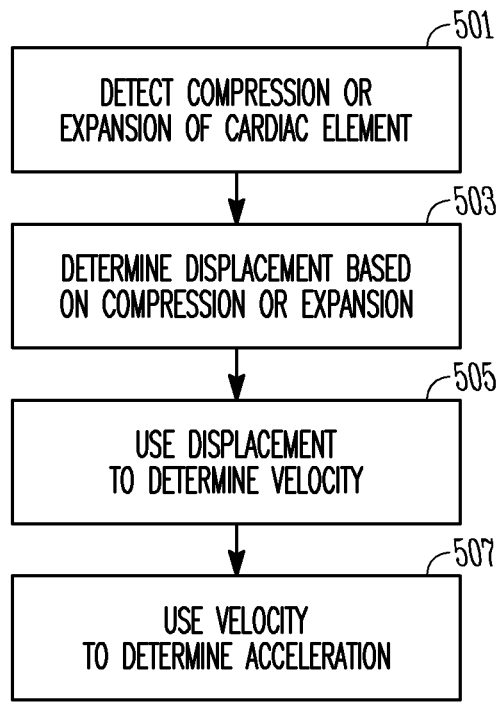
FIG. 5A illustrates an example of measurements derived using one or more sensed forces.
Figure 5B:
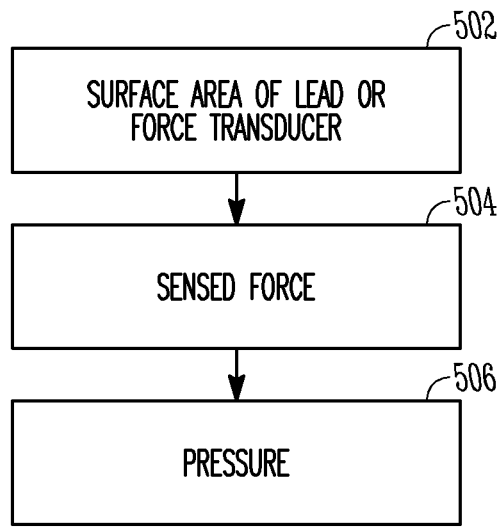
FIG. 5B illustrates an example of measurements derived using the surface areas of one or more leads and one or more sensed forces.

FIG. 5A and FIG. 5B illustrate examples of measurements obtained using a sensed heart wall force. FIG. 5A illustrates measurements obtained using the force sensor. At 501, the a compression or expansion of an cardiac element is determined. At 503, the compression or expansion of the cardiac element is used to determine a displacement indicative of heart motion. At 505, the displacement can optionally be used to determine the velocity of a heart movement, such as by computing a time derivative of the displacement. At 507, the velocity of a heart movement can optionally be used to determine the acceleration of the heart movement, if desired, such as by calculating a time derivative of the velocity with respect to the period of time when the heart movement's force was sensed. Some uses of mechanical characteristics derived from a force sensor such as acceleration, velocity or displacement are described below. Although the example of FIG. 5A has emphasized determining expansion or compression of a cardiac element, and using the determined expansion or compression to derive displacement, velocity, and acceleration, alternatively, a force is sensed or determined as discussed above, and the sensed force is used to determine acceleration, velocity, or displacement. In such examples, the mass of an operative portion of the lead is generally known before its implantation, or such mass can be approximated. The mass and a sensed force can be used to determine a heart wall acceleration, such as by dividing the sensed force by the mass of the operative portion of the lead. The acceleration can also be used to determine a heart wall velocity, such as by integrating the acceleration over the period of time when the heart movement's force was sensed. The velocity can be used to determine the displacement of the heart movement, if desired, such as by calculating a time derivative of the velocity with respect to the period of time when the heart movement's force was sensed.

FIG. 5B illustrates an example of another hemodynamic measurement that can be obtained using a sensed heart wall movement force. At 502, the surface area of the portion of the lead or the force sensor in contact with heart tissue is known, estimated, or determined. At 504, the heart wall force is determined, such as discussed above. At 506, the surface area and the force are used to determine a pressure of the heart movement. Some various uses the measured pressure are described below.

FIG. 6A to FIG. 6H illustrate examples of cardiac monitoring using one or more sensed heart wall forces or characteristics derived therefrom, such as force magnitude, force direction, torsion, or pressure, as well as acceleration, velocity, or displacement. This can provide information about heart function, or can be used in conjunction with (or to qualify or confirm) one or more other indications of heart function, such as one or more sensed electrogram signals, for example. Such information can be communicated to a caregiver, can be automatically processed to indicate hemodynamic status, or can be used to automatically adjust one or more operational parameters of an implantable device.

Figure 6A:
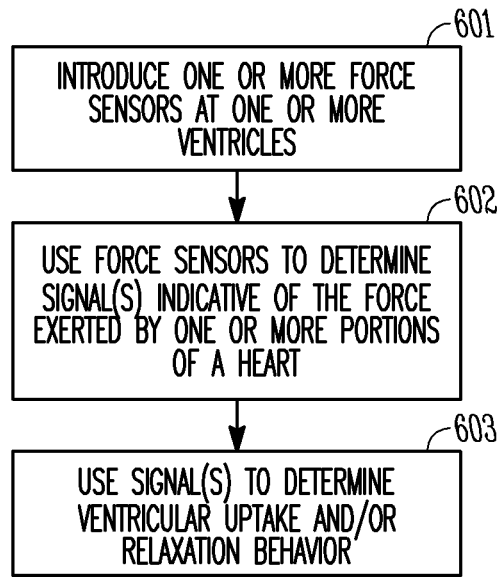
FIG. 6A illustrates generally an example of using one or more sensed forces, such as to determine ventricular uptake behavior or relaxation behavior.

FIG. 6A illustrates an example of determining a ventricular uptake (contraction) or ventricular relaxation (expansion) behavior using the sensed heart wall force or a derived characteristic thereof. In an example, at 601, a ventricular lead includes at least one force sensor to detect a heart wall force (or a derived characteristic of the force) during contraction or expansion. For example, a relative indication of contraction and expansion derived from force can be used as a patient diagnostic indicator, or to control adjustment of one or more therapy control parameter settings, as discussed above.

The force sensor signals can also be processed to determine contraction time, expansion time, a relative figure of merit of the two, or a "pause" time between contraction and expansion. Such information can be used as a patient diagnostic indicator (e.g., by comparison to a threshold value), or to control adjustment of one or more therapy control parameter settings, as discussed above.

A direction or magnitude of an acute or chronic trend in such measurements can also be obtained. Such information can be used as a patient diagnostic indicator (e.g., by comparison to a threshold value), or to control adjustment of one or more therapy control parameter settings, as discussed above.

The force (or derived characteristic) information can also be used in combination with information from an electrogram signal to determine ventricular uptake or relaxation behavior. The electrogram signal includes depolarization information about a ventricular contraction, and repolarization information about a ventricular expansion. For example, a time interval between the onset or peak of the electrogram-indicated ventricular depolarization and the onset or peak of the mechanically-indicated contractive force can provide diagnostic information about the heart contraction. Such information can be used as a patient diagnostic indicator (e.g., by comparison to a threshold value), or to control adjustment of one or more therapy control parameter settings, as discussed above. Similar information can be developed from a time interval between the electrogram-indicated depolarization and the force-indicated ventricular expansion.

Figure 6B:
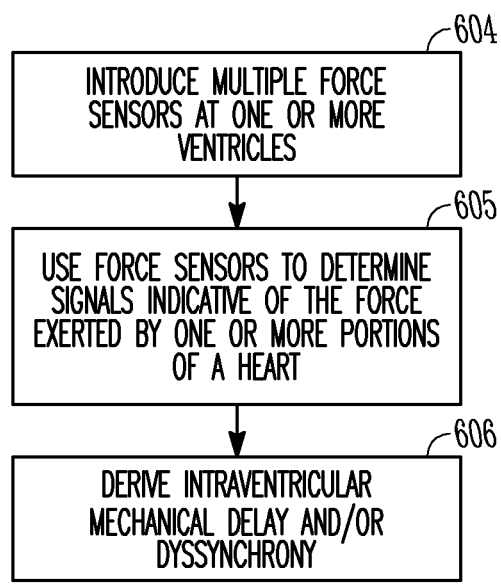
FIG. 6B illustrates generally an example of using one or more sensed forces, such as to determine intraventricular mechanical delay or dyssynchrony.

FIG. 6B illustrates an example of determining at least one of an intraventricular mechanical delay or depolarization sequence) or an intraventricular dyssynchrony, such as by using multiple force sensors at different locations of the same heart chamber. In FIG. 6B, at 605, the force sensors are used to determine respective heart wall force signals. At 606, this information is used to provide an indication of intrachamber mechanical delay or intrachamber dyssynchrony. Such information can be used as a patient diagnostic indicator (e.g., by comparison to a threshold value), or to control adjustment of one or more therapy control parameter settings, as discussed above, such as to reduce or minimize the intrachamber delay or intrachamber dyssynchrony.

For example, a timing between peak contractive forces at such different locations within the same heart chamber can indicate the mechanical contraction delay of that heart chamber at such different locations of that heart chamber. As an illustrative example, a time between peak contractive forces of two right ventricular (RV) force sensors at different RV locations (e.g., RV freewall and RV septum) provides an indication of intraventricular mechanical delay. Another illustrative example includes a left ventricular force sensor (e.g., within a coronary vein) and an RV septum force sensor (e.g., as a proxy, at the common septal wall in RV, for an LV septum force sensor) to provide an indication of intraventricular mechanical delay. Regardless of whether such an intraventricular mechanical delay exists, if a contraction force at a first location of a heart chamber is inappropriate in magnitude or direction relative to a second location of that heart chamber, an intraventricular dyssynchrony exists. Such intraventricular dyssynchrony can be measured using the force sensors at the different locations of the heart chamber, such as by comparing the force at one location to the force at another location, or by computing a ratio, difference, or other relative indication of the forces at the different locations and comparing that relative indication to a certain threshold value. Additionally or alternatively, these examples can provide similar indications for heart chamber expansion forces, rather than heart chamber contractive forces. The measurement of intraventricular delay or intraventricular dyssynchrony can be used to provide a patient diagnostic indicator, or to automatically or otherwise control therapy delivery by the device.

Figure 6C:
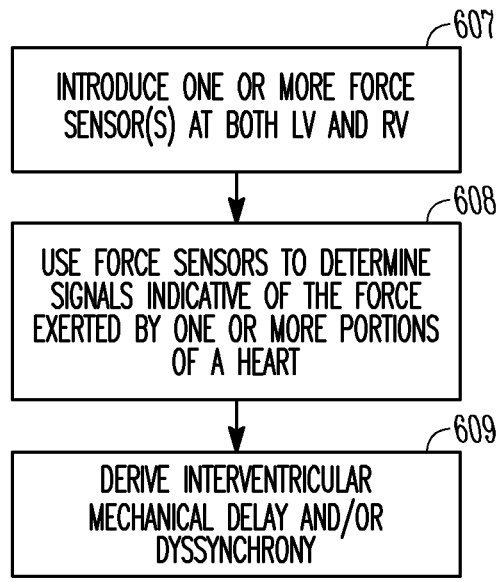
FIG. 6C illustrates generally an example of using one or more sensed forces, such as to determine interventricular mechanical delay or dyssynchrony.

FIG. 6C illustrates an example of determining at least one of an interventricular mechanical delay and interventricular dyssynchrony. In this example, at 607, one or more leads are introduced, such that there is one or more force sensors associated with each of the right and left ventricles. At 608, the one or more force sensors are used to determine one or more signals indicative of one or more forces exerted by one or more portions of a heart. At 609, the signals indicative of sensed force are used to determine at least one of an interventricular mechanical delay and an interventricular dyssynchrony.

For example, a timing between occurrences of peak contractive forces at different locations in different heart chambers can indicate the mechanical delay of the contraction between heart chambers. As an illustrative example, a time between a peak contractive force of an RV force sensor and a peak contractive force of an LV force sensor will provide an indication of interventricular mechanical delay. Regardless of whether such an interventricular mechanical delay exists, if an RV contraction force is inappropriate in magnitude or direction relative to an LV contraction force, an interventricular dyssynchrony exists. Such interventricular dyssynchrony can be measured using the RV and LV force sensors, such as by comparing the RV and LV forces, or by computing a ratio, difference, or other relative indication of the RV and LV forces and comparing that relative indication to a threshold value. Additionally or alternatively, these examples can provide similar indications for heart chamber expansion forces, rather than heart chamber contractive forces. The measurement of interventricular delay or interventricular dyssynchrony can be used to provide a patient diagnostic indicator, or to automatically or otherwise control therapy delivery by the device.

If the interventricular mechanical delay or interventricular dyssynchrony exists, one or more bi-ventricular pacing or other response parameters (e.g., electrostimulation voltage, electrode selection for electrostimulation, LV offset (timing between LV and RV paces) or the like) may be initiated or adjusted, either automatically or by user-programming.

The interventricular mechanical delay or interventricular dyssynchrony can be measured using the force signals, or one or more characteristics derived from such force signals, such as acceleration, velocity, displacement, or pressure. For example, a time derivative of pressure (DP/DT) can provide an indicator of interventricular dyssynchrony.

Figure 6D:
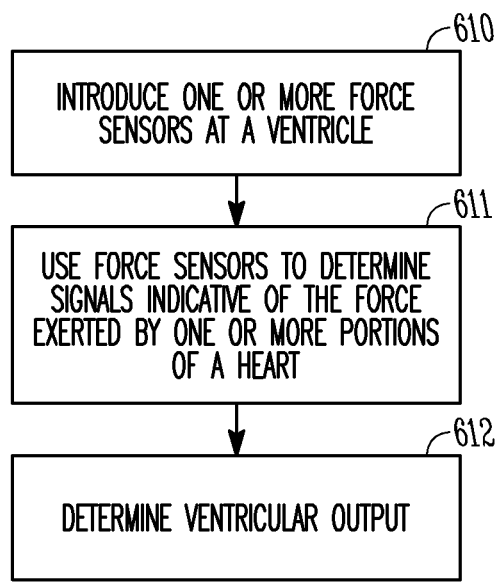
FIG. 6D illustrates generally an example of using one or more sensed forces, such as to determine ventricular output.

FIG. 6D illustrates an example of determining a ventricular output. In this example, at 610, one or more leads are placed in a ventricle. At 611, one or more lead-based force sensors are used to determine one or more signals indicative of one or more ventricular heart wall forces. At 612, the one or more forces are used to determine an indication of ventricular output, such as stroke volume. Ventricular output can be determined by multiplying the stroke volume by the heart rate. The heart rate can be obtained by processing the signal from the one or more force sensors or the electrogram signal from an cardiac signal sensor. A force sensor located at a ventricular freewall can be used to measure heart wall displacement during a contraction. If the volume of the heart in a relaxed state is known or can be estimated, the contractive displacement of the heart wall can be used to approximate the volume of blood expelled during the heart contraction. The heart rate and the stroke volume can be used to approximate a ventricular cardiac output.

Figure 6E:
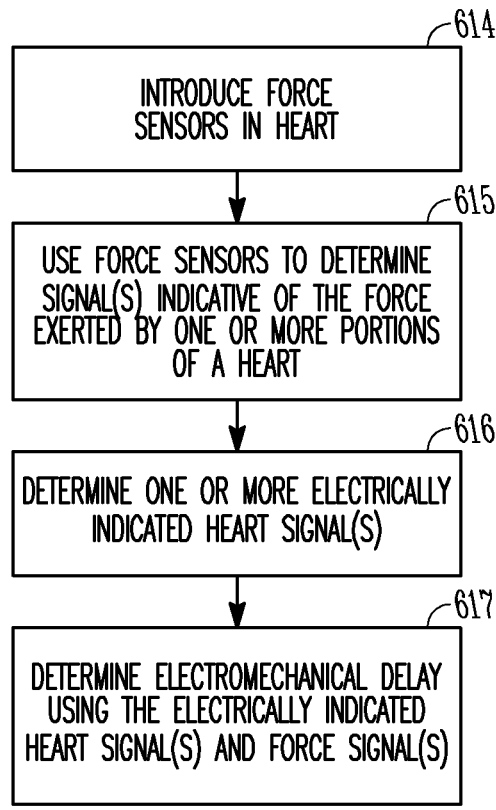
FIG. 6E illustrates generally an example of using one or more sensed forces, such as to determine electromechanical delay.

FIG. 6E illustrates an example of sensing one or more heart wall forces and one or more electrogram signals and determining an electromechanical delay, such as a time delay between an electrical depolarization and a resultant heart contraction. At 614, one or more leads including one or more force sensors are placed in a heart. At 615, the one or more force sensors are used to determine one or more signals indicative of one or more heart wall forces. At 616, one or more electrogram signals are determined. At 617, an electromechanical delay is assessed using the one or more electrogram signals and the one or more force signals. Such information can be used as a patient diagnostic indicator (e.g., by comparison to a threshold value), or to control adjustment of one or more therapy control parameter settings, as discussed above.

Figure 6F:
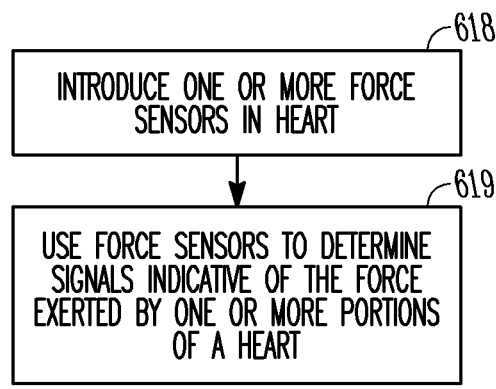
FIG. 6F illustrates generally an example of using one or more sensed forces, such as to determine an evoked response.

FIG. 6F illustrates an example of determining at least one of a pacing or other electrostimulation energy or delivery location. At 618, one or more leads including one or more force sensors are placed in a heart. At 619, the one or more force sensors are used to determine one or more signals indicative of one or more heart wall forces. This information is used to determine at least one of a pacing or other electrostimulation energy or delivery location. For example, if the force sensors indicate that a first portion of a heart chamber is contracting with a substantially greater force than a second portion of that heart chamber, a electrode closer to the second portion of the heart chamber could be selected (or its time of electrostimulation delivery slightly advanced) to resynchronize the heart chamber contraction based on the sensed force information.

Such information can be obtained from an intrinsic heart contraction, or from an evoked response to one or more delivered electrostimulations. In addition or as an alternative to adjusting a cardiac resynchronization parameter, the evoked response information can be used, for example, in an autothreshold or autocapture technique, such as to reduce or adjust electrostimulation energy, such as to promote longevity of the implanted device.

Figure 6G:
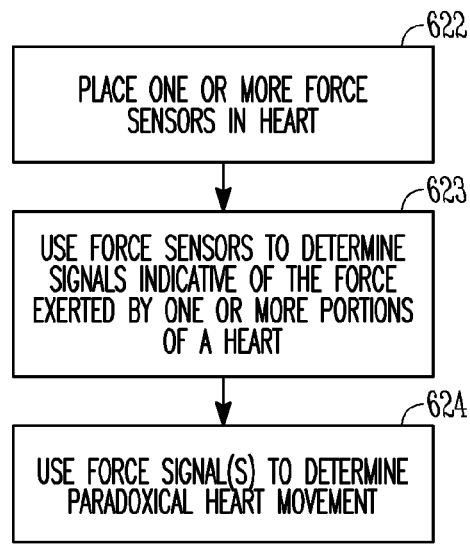
FIG. 6G illustrates generally an example of using one or more sensed forces, such as to determine a paradoxical heart movement.

FIG. 6G illustrates an example of detecting a paradoxical heart movement. In this example, at 622, one or more leads including one or more force sensors are introduced into a heart. At 623, the one or more force sensors are used to determine one or more signals indicative of one or more forces exerted by one or more portions of a heart. At 624, the one or more force signals are used are used to detect a paradoxical heart movement. For example, a force sensor can be placed at a ventricular septum, which separate right and left ventricles. If the force sensors detect that heart contractions result in a substantial amount of septal movement (e.g., back and forth between the right and left ventricles), this can indicate poor RV-LV synchronization. In another example, force sensors can be placed at different locations on a ventricular freewall to detect a paradoxical heart movement in which a weakened portion of the heart bulges outward during a contraction rather than moving inward during the contraction, as would normally be expected. This paradoxical movement may result from heart tissue scarring resulting from a myocardial infarction. Thus, when one portion of a ventricular freewall exerts force in a different direction than other portions, this may indicate a paradoxical heart movement. In certain examples, heart tissue scarring may result in a portion of the heart moving slightly or not at all during a contraction. This may also indicate a paradoxical heart movement. Such information can be used as a patient diagnostic indicator (e.g., by comparison to a threshold value), or to control adjustment of one or more therapy control parameter settings, as discussed above.

Figure 6H:
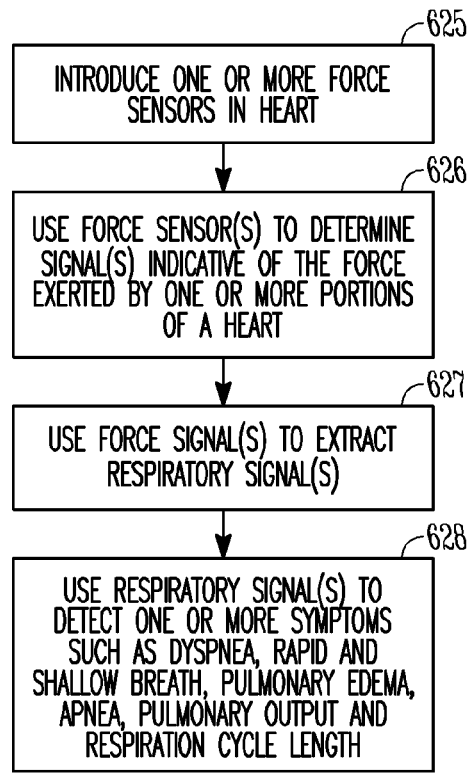
FIG. 6H illustrates generally an example of using one or more sensed forces, such as to determine one or more respiratory signals.

FIG. 6H illustrates an example of determining at least one respiratory signal. In this example, at 625, one or more leads are used to introduce one or more force sensors into a heart. At 626, the one or more force sensors are used to determine one or more heart wall force signals. At 627, one or more respiratory signals are extracted from the one or more force signals. Breathing causes the lungs to exert a force on the heart, which can be detected by an cardiac force sensor as part of the heart wall force signal. Breathing typically occurs at a lower frequency than heart rate, therefore, a lowpass filter can be used to extract the breathing information from the heart wall force signal. The lowpass filter can have an adaptive cutoff frequency, which is adjusted as a function of heart rate as determined from the heart wall force signal or an electrogram signal. At 628, the one or more extracted respiratory signals can be used to detect one or more respiratory symptoms or indications such as dyspnea, rapid and shallow breathing, apnea, or respiration cycle length. Detection of such respiratory symptoms can make use of other physiological information, for example, obtained from one or more other physiological sensors, such as a sleep detector, a posture detector, or the like.

Figure 7A:
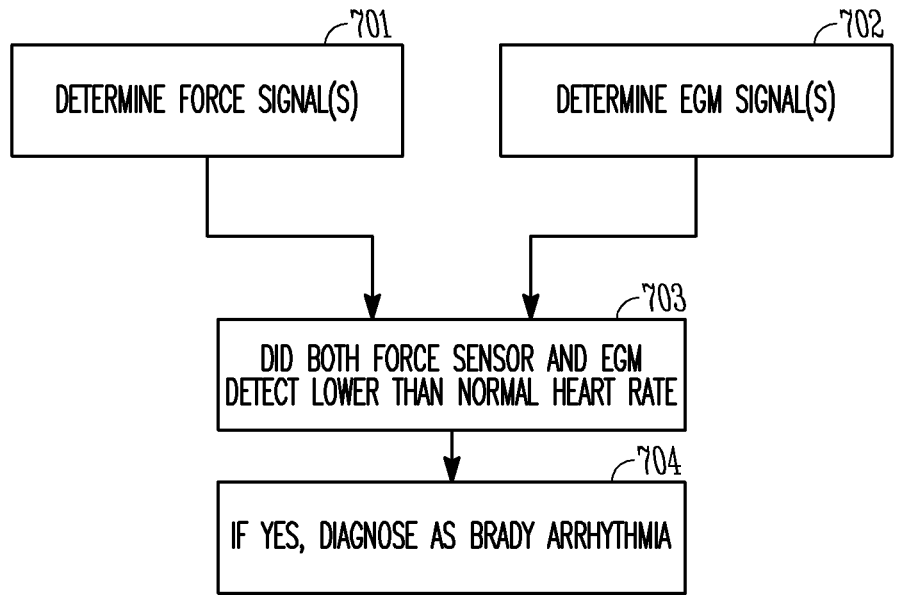
FIG. 7A illustrates generally an example of using one or more sensed forces, such as to determine a bradyarrhythmia.
Figure 7B:
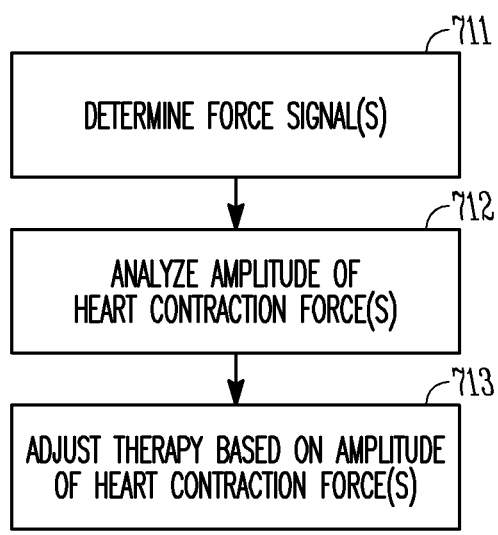
FIG. 7B illustrates generally an example of using one or more sensed forces, such as to determine a tachyarrhythmia.

FIG. 7A and FIG. 7B illustrate various examples of detecting an indication of an arrhythmia at least in part by using one or more sensed cardiac forces. FIG. 7A illustrates an example of using one or more force sensors to provide information to diagnose or treat a bradyarrhythmia. In this example, at 701, one or more signals indicative of cardiac force are sensed. At 702, one or more electrogram (EGM) signals are sensed. At 703, the force signal is compared to the electrogram signal. At 704, a bradyarrhythmia condition may be declared when both the electrogram signal and the sensed one or more forces detect one or more missing beats. A bradyarrhythmia condition may also be declared when both the electrogram signal and the sensed one or more forces detect a lower than normal heart rate.

FIG. 7B illustrates an example of using one or more force sensors to diagnose or treat tachyarrhythmia. In the example of FIG. 7B, at 711, one or more signals indicative of force are determined. At 712, the amplitude of the force of the heart contraction is analyzed. At 713, therapy is adjusted based on the amplitude, such as by comparing the peak contractive force amplitude to one or more threshold values. If the amplitude is high enough, it is inferred that the heart is still performing adequately in pumping blood, even if a tachyarrhythmia has been declared using other techniques (e.g., heart rate exceeds a threshold, depolarization morphology indicates tachyarrhythmia, etc.). Therefore, because the force sensor indicates adequate cardiac output, anti-tachyarrhythmia therapy is withheld, or anti-tachyarrhythmia pacing is delivered rather than a more painful defibrillation shock. Conversely, if the force sensor indicates weak contractions, from which inadequate cardiac output can be inferred, then such unstable hemodynamic status triggers a more aggressive response, such as immediate or quick delivery of a defibrillation shock. In another example, the frequency of heart contractions is determined using the signals indicative of force. In this example, anti-tachyarrhythmia therapy is initiated or adjusted in response to the frequency of the heart contractions.

Figure 8:
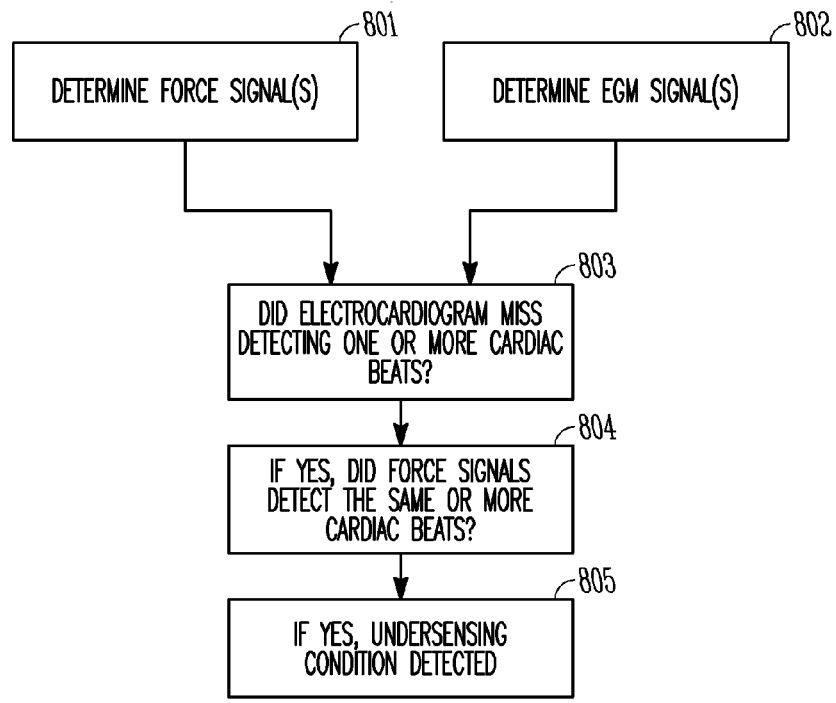
FIG. 8 illustrates generally an example of using one or more sensed forces, such as to determine whether undersensing exists.

FIG. 8 illustrates an example of detecting an electrical depolarization undersensing condition. At 801, one or more signals indicative of cardiac force are used to detect heart contractions. At 802, one or more electrogram (EGM) signals are used to detect heart contractions. If a contraction is detected by the force sensor, but not by the electrogram signal the electrical depolarization undersensing condition can be declared. Alternatively, at 803, the electrogram signal is analyzed to determine if one or more cardiac contraction is missed during an expected time window of occurrence. If no cardiac contractions are missed when expected, then an undersensing condition is not declared. However, if the electrogram signal indicates that a cardiac contraction is missed, then at 804 one or more force signals are analyzed to determine if the missed contraction is present. At 805, if the one or more force signals indicates the presence of at least one contraction that is absent from the sensed electrogram signal, an electrical depolarization undersensing condition is declared. Undersensing of electrical depolarizations can cause an incorrect diagnosis of bradyarrhythmia or tachyarrhythmia, resulting in inappropriate delivery or withholding of anti-arrhythmia therapy. The cardiac force-derived contraction information can be used to augment the electrogram-derived information, or the undersensing can be reported to the user so that one or more sensing parameters can be adjusted to avoid future undersensing. Alternatively, automatic adjustment of one or more sensing parameters can be performed in response to the undersensing condition, for example, until such undersensing condition is resolved.

Figure 9:
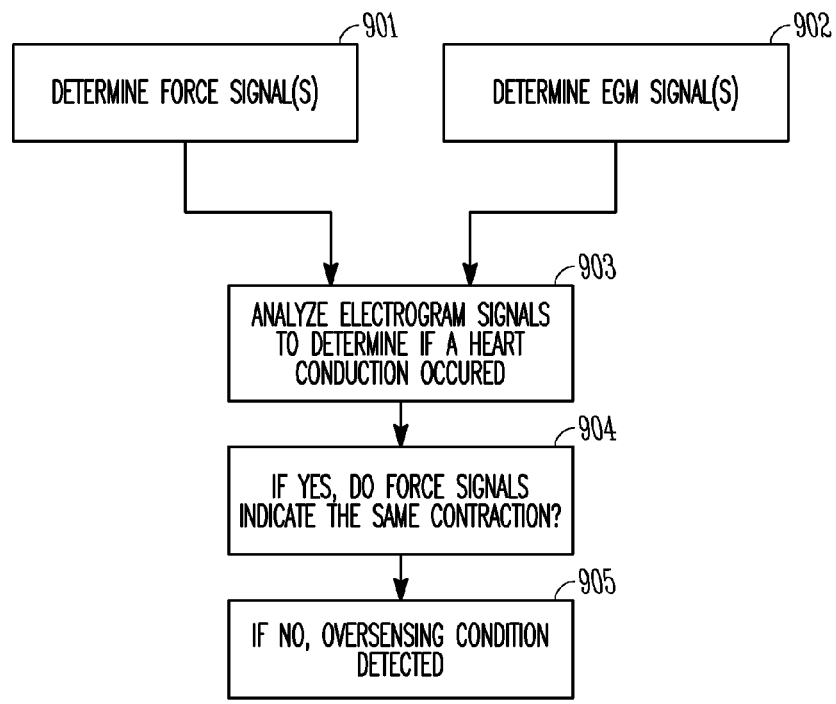
FIG. 9 illustrates generally an example of using one or more sensed forces, such as to determine whether oversensing exists.

FIG. 9 illustrates an example of determining an electrical depolarization oversensing condition. At 901, one or more signals indicative of cardiac force are obtained. At 902, one or more electrogram (EGM) signals are obtained. At 903, electrically-indicated contractions are extracted from depolarizations in the electrogram signal. At 904, force-indicated contractions are extracted from the one or more cardiac force signals. At 905, if the electrogram signal exhibits one or more contractions that are not present in the force signal, then an electrical depolarization oversensing condition can be declared. Oversensing of electrical depolarizations can cause an incorrect arrhythmia diagnosis, resulting in inappropriate delivery or withholding of anti-arrhythmia therapy. The cardiac force-derived contraction information can be used to qualify the electrogram-derived information, or the oversensing can be reported to the user so that one or more sensing parameters can be adjusted to avoid future oversensing. Alternatively, automatic adjustment of one or more sensing parameters can be performed in response to the oversensing condition, for example, until such oversensing condition is resolved.

Figure 10:
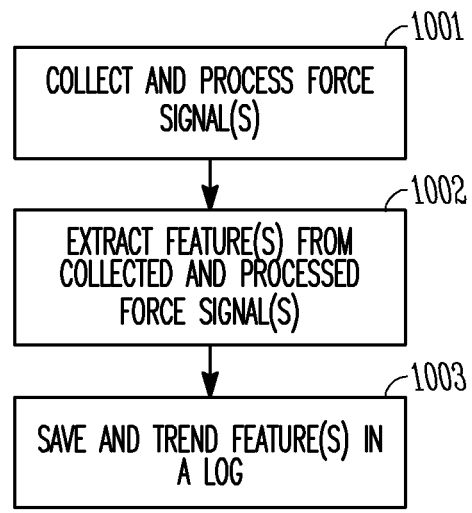
FIG. 10 illustrates an example of trending cardiac measurements.

FIG. 10 illustrates an example of collecting, aggregating, or using one or more signals indicative of cardiac force, or one or more features extracted therefrom. At 1001, one or more force signals from one or more cardiac force sensors are acquired. At 1002, one or more features are extracted from the one or more cardiac force signals. Examples of such features can include, by way of example, but not by way of limitation: a minimum value, a maximum value, a minimum time rate of change, a maximum time rate of change, a mean value, a mean time rate of change, a median value, a median time rate of change, a positive change in force over change in time (e.g., during systole), a negative change in force over change in time (e.g., during diastole), a systolic time duration, or a diastolic time duration. At 1003, one or more of these features are stored and trended in a log, which can track such information over many cardiac cycles. In various examples, the log can also store information about ventricular uptake and relaxation behavior, intraventricular or interventricular mechanical delay or dyssynchrony, ventricular output, one or more indications derived from respiratory signals, one or more conditions of bradyarrhythmia, tachyarrhythmia, oversensing, undersensing, or other conditions indicative of patient health. The trended data can be saved in the implantable medical device 204 or communicated to a remote or local external device, such as an external programmer or a remote server. In certain examples, if one or more changes in such extracted features exceed one or more corresponding thresholds, an alert can be generated and/or delivered, such as to a physician, patient, or other user.

Although the above description has emphasized sensing force, the present force sensor techniques also permit sensing of displacement or motion, which is also useful for the various applications discussed herein.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A method comprising:
   sensing one or more forces exerted by at least a portion of a heart by detecting a compression or expansion of an implanted intracardiac element;
   obtaining sensed force signal responsive to the one or more forces by measuring a displacement of the compression or expansion of the implanted intracardiac element, wherein the implanted intracardiac element includes a force sensor including:
   a displacement sensor configured to sense a displacement of the portion of the heart during a heart movement, the displacement sensor including a first portion movable with respect to a second portion along an axial direction and in response to the displacement of the portion of the heart axial movement of the first portion with respect to the second portion being representative of the displacement of the portion of the heart, the displacement sensor being configured to provide an output displacement signal indicative of the displacement sensed; and
   a contractile structure separate from the displacement sensor, the contractile structure being configured to axially expand or axially contract an axial distance representative of the axial movement of the first portion of the displacement sensor with respect to the second portion, wherein the force sensor is configured to provide the sensed force signal indicative of a force with which at least the portion of the heart moves during the heart movement, the force sensor configured to determine the force as a function of the distance that the contractile structure axially expands or axially contracts; and communicating sensed force signal to an electronics unit of an implantable medical device.

2. The method of claim 1, wherein sensing the one or more forces exerted by at least the portion of the heart by detecting the compression or expansion of the implanted intracardiac element includes using the force sensor of the implanted intracardiac element, the force sensor associated with a distal portion of a fully implantable intravascular cardiac lead of the implanted intracardiac element.

3. The method of claim 1, comprising determining a value of the one or more forces exerted by at least the portion of the heart by using a force-displacement relationship of the implanted intracardiac element and the displacement of the compression or expansion.

4. The method of claim 3, comprising determining a pressure exerted on the implanted intracardiac element by at least the portion of the heart using the sensed one or more forces exerted by at least the portion of the heart.

5. The method of claim 1, comprising selecting at least one of a pacing voltage and a pacing location based on the sensed one or more forces exerted by at least the portion of the heart.

6. The method of claim 1, comprising determining a paradoxical heart movement using the sensed one or more forces exerted by at least the portion of the heart.

7. The method of claim 1, comprising:
storing an indication of the electrical signal over more than one cardiac cycle; and
detecting a change in the indication of the electrical signal over a time period that spans more than one cardiac cycle.

8. The method of claim 1, comprising determining at least one of a minimum value, a maximum value, a minimum time rate of change, and a maximum time rate of change of the sensed one or more forces.

9. The method of claim 1, comprising determining an undersensing condition, the determining the undersensing condition including:
sensing an electrogram signal to detect electrical cardiac conduction; and
declaring the undersensing condition to exist when the sensed one or more forces indicates at least one conduction that is absent from the sensed electrogram signal.

10. The method of claim 1, comprising determining an oversensing condition, the determining the oversensing condition including:
sensing an electrogram signal to detect electrical cardiac conduction; and
declaring the oversensing condition to exist when the sensed one or more forces indicate an absence of a mechanically-indicated contraction corresponding to at least one electrically-indicated contraction.

11. A method comprising:
sensing a force exerted by a portion of a heart using a force sensor associated with an implanted intracardiac element, the force sensor including:
a displacement sensor configured to sense a displacement of the portion of the heart during a heart movement, the displacement sensor including a first portion movable with respect to a second portion along an axial direction of a portion of the implanted intracardiac element and in response to the displacement of the portion of the heart, axial movement of the first portion with respect to the second portion being representative of the displacement of the portion of the heart, the displacement sensor being configured to provide an output displacement signal indicative of the displacement sensed; and
a contractile structure separate from the displacement sensor, the contractile structure being configured to axially expand or axially contract an axial distance representative of the axial movement of the first portion of the displacement sensor with respect to the second portion, wherein the force sensor is configured to provide a sensed force signal indicative of a force with which at least the portion of the heart moves during the heart movement, the force sensor configured to determine the force as a function of the distance that the contractile structure axially expands or axially contracts; and
communicating the sensed force signal to an electronics unit of an implantable medical device.

12. The method of claim 11, wherein sensing the force includes sensing the force using the force sensor associated with a distal portion of a fully implantable intravascular cardiac lead of the implanted intracardiac element.

13. The method of claim 11, comprising determining the force with which the portion of the heart moves using a specified force-displacement relationship of the contractile structure.

14. The method of claim 11, comprising initiating or adjusting a delivered electrical energy or a delivered substance in response to the sensed force signal.

15. The method of claim 11, comprising using the sensed force signal to determine at least one of:
a ventricular uptake;
a ventricular relaxation behavior;
an interventricular mechanical delay;
an interventricular dyssynchrony;
a ventricular output;
an electromechanical delay;
an evoked response;
a pacing voltage;
a pacing location;
a paradoxical movement; and
a respiratory signal.

16. A method comprising:
sensing a force exerted by a portion of a heart using a force sensor associated with an implanted intracardiac element, the force sensor including:
a displacement sensor configured to sense a displacement of the portion of the heart during a heart movement, the displacement sensor being configured to provide an output displacement signal indicative of the displacement sensed, the force sensor including a first portion movable with respect to a second portion along an axial direction and in response to the displacement of the portion of the heart, axial movement of the first portion with respect to the second portion being representative of the displacement of the portion of the heart; and
a contractile structure separate from the displacement sensor, the contractile structure being configured to axially expand or axially contract an axial distance representative of the displacement sensed by the displacement sensor, wherein the force sensor is configured to provide a sensed force signal indicative of a force with which at least the portion of the heart moves during the heart movement, the force sensor configured to determine the force as a function of the distance that the contractile structure axially expands or axially contracts, wherein the contractile structure is configured to axially expand or axially contract the axial distance representative of the axial movement of the first portion of the displacement sensor with respect to the second portion.

17. The method of claim 16, comprising communicating the sensed force signal to an electronics unit of an implantable medical device, wherein sensing the force includes sensing the force using the force sensor associated with a distal portion of a fully implantable intravascular cardiac lead of the implanted intracardiac element.

18. The method of claim 16, comprising determining a paradoxical movement of the heart using the sensed force signal.

19. The method of claim 16, comprising initiating or adjusting a delivered electrical energy or a delivered substance in response to the sensed force signal.

20. The method of claim 16, comprising using the sensed force signal to determine at least one of:
   a ventricular uptake;
   a ventricular relaxation behavior;
   an interventricular mechanical delay;
   an interventricular dyssynchrony;
   a ventricular output;
   an electromechanical delay;
   an evoked response;
   a pacing voltage;
   a pacing location; and
   a respiratory signal.

21. A method comprising:
   sensing one or more forces exerted by at least a portion of a heart by detecting a compression or expansion of an implanted intracardiac element;
   obtaining a sensed force signal responsive to the one or more forces by measuring a displacement of the compression or expansion of the implanted intracardiac element, the obtaining including:
      sensing a displacement of a first element of the implanted intracardiac element with respect to second element of the implanted intracardiac element along an axial direction and in response to a displacement of the portion of the heart;
      sensing an axial contraction of a contractile structure of the implanted intracardiac element separate from the first element and the second element; and
      using the sensed displacement and the sensed axial contraction information to determine the sensed force signal; and
   communicating the sensed force signal to an electronics unit of an implantable medical device.

* * * * *